(12) United States Patent
Han

(10) Patent No.: US 7,999,092 B2
(45) Date of Patent: Aug. 16, 2011

(54) AMPLICON RESCUE MULTIPLEX POLYMERASE CHAIN REACTION FOR AMPLIFICATION OF MULTIPLE TARGETS

(75) Inventor: Jian Han, Huntsville, AL (US)

(73) Assignee: HudsonAlpha Institute for Biotechnology, Huntsville, AL (US)

( * ) Notice: Subject to any disclaimer, the term of this patent is extended or adjusted under 35 U.S.C. 154(b) by 0 days.

(21) Appl. No.: 12/418,532

(22) Filed: Apr. 3, 2009

(65) Prior Publication Data

US 2009/0253183 A1    Oct. 8, 2009

Related U.S. Application Data

(60) Provisional application No. 61/042,259, filed on Apr. 3, 2008.

(51) Int. Cl.
*C07H 21/02* (2006.01)
(52) U.S. Cl. ...................................... 536/23.1; 435/975
(58) Field of Classification Search ........................ None
See application file for complete search history.

*Primary Examiner* — Christopher M. Babic
(74) *Attorney, Agent, or Firm* — Donna Russell

(57) ABSTRACT

Disclosed is a method for amplifying and detecting polynucleotides which can provide sensitive, specific detection of multiple targets from a clinical specimen within a relatively short time.

1 Claim, 1 Drawing Sheet

AMPLICON RESCUE MULTIPLEX POLYMERASE CHAIN REACTION FOR AMPLIFICATION OF MULTIPLE TARGETS

CROSS-REFERENCE TO RELATED APPLICATIONS

This application claims the benefit of priority of U.S. Provisional Patent Application No. 61/042,259, filed Apr. 3, 2008.

FIELD OF THE INVENTION

The invention relates generally to methods for amplifying nucleic acids. More specifically, the invention relates to methods for using the polymerase chain reaction to amplify multiple nucleic acid sequences.

BACKGROUND OF THE INVENTION

The development of the polymerase chain reaction (PCR) enabled the use of DNA amplification for a variety of uses, including molecular diagnostic testing. There are challenges associated with the use of PCR for molecular differential diagnostic (MDD) assays, however. PCR utilizes specific primers or primer sets, temperature conditions, and enzymes. PCR reactions may easily be contaminated, primer binding may require different conditions for different primers, primers should be specific for a target sequence in order to amplify only that target sequence, etc. This has made it even more difficult to amplify multiple sequences from a single sample.

Diagnostic testing of clinical samples to find one or more causative disease agents has, in the past, required that microorganisms be isolated and cultured. This may take days, however, and in many cases a diagnosis must be acted upon within hours if the patient's life is to be saved. Analysis of a single clinical sample to identify multiple organisms in order to determine which one(s) may be the causative agent(s) of disease is the desired method for MDD, and methods have been developed to better achieve that goal. For example, multiplex PCR methods have been developed to amplify multiple nucleic acids within a sample in order to produce enough DNA/RNA to enable detection and identification of multiple organisms. Multiplex PCR has disadvantages, however. For example, each target in a multiplex PCR reaction requires its own optimal reaction conditions, so increasing the number of targets requires that the reaction conditions for each individual target are less than optimal. Furthermore, multiple sets of high-concentration primers in a system often generate primer dimmers or give non-specific, background amplification. This lack of specificity also requires the additional steps of post-PCR clean-up and multiple post-hybridization washes. Crowded primers reduce the amplification efficiency by requiring the available enzymes and consuming substrates. Differences in amplification efficiency may lead to significant discrepancies in amplicon yields. For example, some loci may amplify very efficiently, while others amplify very inefficiently or fail to amplify at all. This potential for uneven amplification also makes it difficult to impossible to accurately perform end-point quantitative analysis.

One method utilizes nested gene-specific primers used at very low concentrations to enrich the targets during the initial PCR cycling. Later, common primers are used to amplify all the targets. The entire reaction is performed in one tube, no additional rounds of PCR are required, and it does not require specialized instruments but may instead be performed using regular thermal cyclers. There are disadvantages to this method, however. For example, because a low concentration of primers is used to enrich the targets during the initial cycles, the sensitivity of the assay is ultimately decreased, the initial enrichment cycles require longer annealing time for each cycle, and the enzyme is more likely to be less efficient over the number of cycles required to amplify the target.

A need still exists for more sensitive, faster, and more efficient methods for amplifying DNA and/or RNA from multiple targets to promote rapid identification of those targets.

SUMMARY OF THE INVENTION

The present invention relates to a method for amplifying nucleic acids to enable detection of those nucleic acids, the method comprising the steps of amplifying one or more target nucleic acids using high concentration, target-specific primers in a first amplification reaction, thereby producing at least one nucleic acid amplicon containing at least one common primer binding site; rescuing the at least one nucleic acid amplicon; and amplifying the at least one nucleic acid amplicon in a second amplification reaction utilizing common primers which bind to the at least one common primer binding site. One aspect of the invention utilizes nested target-specific primers. Target nucleic acids may comprise DNA and/or RNA, and may comprise DNA and/or RNA of viral, bacterial, and/or fungal origin, as well as genomic DNA and/or RNA of human or other animal origin. Amplification may be performed by polymerase chain reaction (PCR) and/or RT-PCR. The source of the target nucleic acids may be from one or more clinical, environmental, or food samples and the method may be used in a wide variety of ways, including, for example, clinical diagnosis, environmental sampling, plant testing, food safety analysis, detection of genetic disorders, and/or detection of disease conditions. The method may be used for human and/or veterinary medical diagnoses.

DETAILED DESCRIPTION

Figure 1:
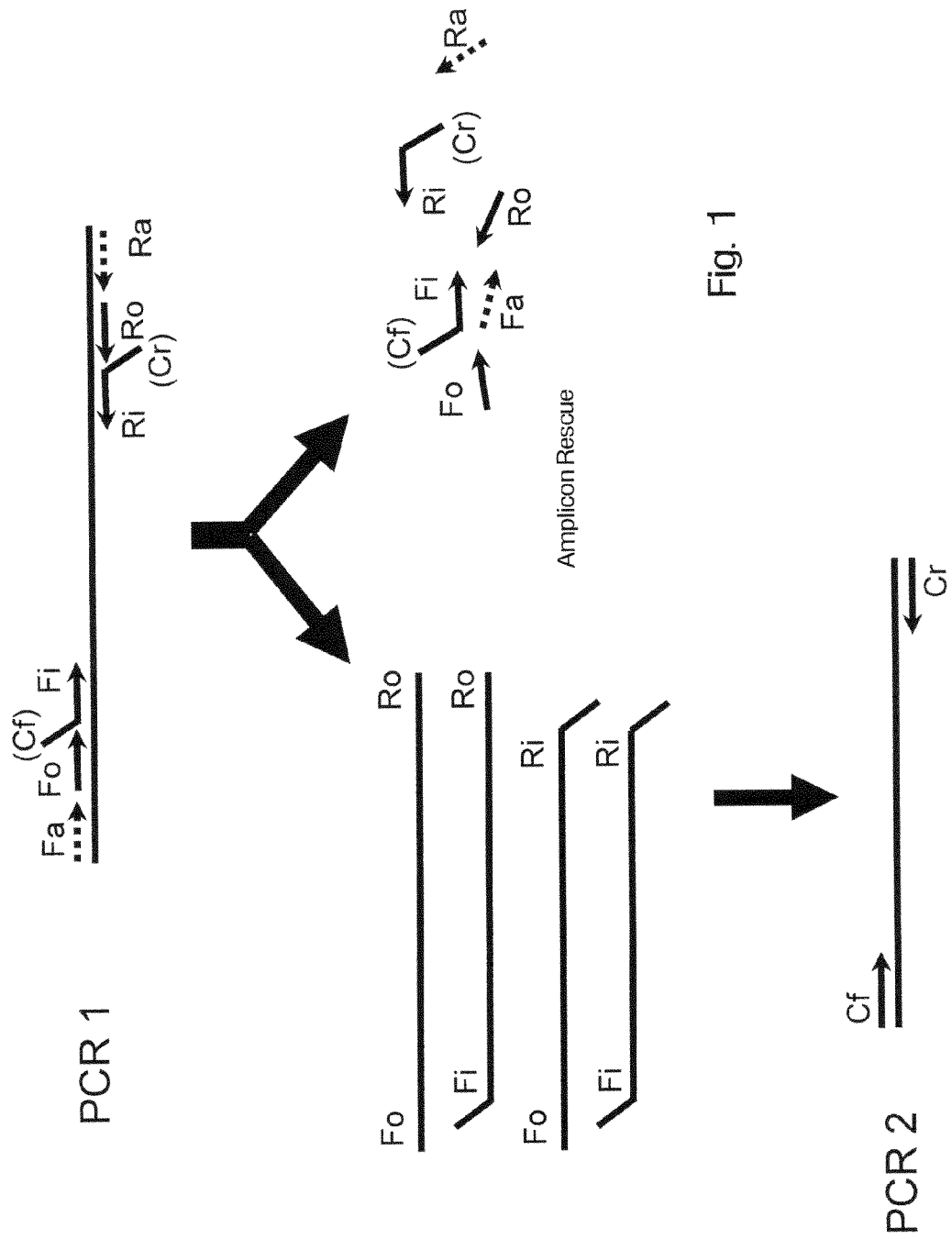
FIG. 1 is an illustration of the method of the invention, where $F_o$ represents forward-out primers; $F_i$ represents forward-in primers with a forward common primer tag (binding sequence); $C_f$ represents a forward common primer; $R_i$ represents a reverse-in primer with reverse common primer tag (binding sequence); $R_o$ represents a reverse-out primer; $C_r$ represents a reverse common primer; $F_a$ represents an additional forward primer; and $R_a$ represents an additional reverse primer, with these primers being positioned generally as indicated.

The inventor has developed a new method for amplifying nucleic acids that may be used to detect the presence, and relative amounts present, of nucleic acids from viruses, bacteria, fungi, plant and/or animal cells for the evaluation of medical, environmental, food, and other samples to identify microorganisms and other agents within those samples. The method will be referred to herein as amplicon rescue multiplex polymerase chain reaction ("arm-PCR"). In this method, PCR amplifications of target nucleic acids are performed sequentially in two different reaction systems. These systems may comprise separate columns, reaction containers, or sections of a chip, for example, containing the target nucleic acid(s), primers, enzymes, nucleotides (e.g., dNTPs) and buffers necessary to amplify the target nucleic acid(s) to produce amplicons. By using high concentration primers in the first amplification reaction and rescuing the amplicons formed during that reaction for use in a second amplification reaction in a different reaction system, the inventor has developed a method that increases sensitivity and specificity, decreases the time needed to produce a detectable result, and readily lends itself to automation.

It is to be understood that the term "comprising," as used herein, may be substituted with the terms "consisting essentially of" and "consisting of." Where the term "reaction system" is used, it is intended to describe an Eppendorf tube, reaction chamber, or other containment device into which the necessary primers, enzymes, nucleotides, buffers, and/or other reagents are placed in order to perform one or more cycles of at least one polymerase chain reaction. A different "reaction system" may therefore refer to the same reaction containment vessel, but a different component of reagents—particularly primers—for performing the desired amplification step. A "reaction containment vessel" is intended to mean a tube, plate well, or other vessel having a sufficient internal volume to contain primers, enzymes, nucleotides, buffers, and/or other reagents necessary to provide a reaction system. The term "rescue" is intended to mean the separation of amplicons from at least a portion of the primers of the first amplification. "PCR" is intended to mean the polymerase chain reaction, and may include PCR and/or RT-PCR procedures.

In the first step of the method, high-concentration, target-specific, nested primers are used to perform a target-specific first amplification procedure. Primers are chosen from known sequences of viruses, bacteria, fungi, and/or other targets for which identification using nucleic acid detection is desired, and are specific for those target nucleic acids and/or closely related target nucleic acids. Target-specific primers may be used to amplify one or more (and preferably multiple) target nucleic acids of bacterial, viral, fungal, and/or other origin, for example. Nested primer concentration may generally be between 5-50 pmol. As illustrated in FIG. 1, selected primers are "tagged" with additional nucleotides to provide an additional sequence that is not specific for the target nucleic acid(s) so that amplification of the target nucleic acid with such a primer will also incorporate into the resulting amplicon a binding site for a common primer that, unlike a target-specific primer, may be used to further amplify unrelated target nucleic acid amplicons (see A and B in FIG. 1). Amplification is performed for approximately 10-15 cycles, the reaction is terminated, and the resulting amplicons are rescued from the reaction mix for use in a second, target-independent amplification procedure, comprising a polymerase chain reaction primed by common primers which will, in a relatively indiscriminate manner, provide amplification of unrelated nucleotide sequences represented by the variety of amplicons rescued from the target-specific reaction.

Amplicon rescue is then performed to minimize or eliminate the primers of the first reaction, while providing amplicons for use in the second amplification using common primers. Amplicon rescue may be performed in a variety of ways. For example, a small sampling from the completed first amplification reaction may be taken to provide amplicons for the second amplification. When a small sample is taken, it provides sufficient numbers of amplicons for the second amplification, while significantly decreasing (e.g., diluting) the remaining numbers of primers of the first amplification. Amplicon rescue may also be performed by removing a significant portion of the contents of the reaction system of the first amplification and adding to the remaining contents the common primer(s) with the necessary enzyme(s), nucleotides, buffer(s), and/or other reagents to perform a second amplification utilizing the common primer(s) to amplify the rescued amplicons in a second reaction system. Separation techniques may also be utilized to rescue amplicons. Such techniques may rely on size differences between the primers and amplicons, on tags that have been attached to the amplicons, the primers, or both, or other methods known to those of skill in the art. Once separated, all of the rescued amplicons or a part of the rescued amplicons may be used in the second amplification.

The second amplification is performed in a different reaction system, which may or may not utilize the same reaction containment vessel. The second amplification amplifies the rescued amplicons using fresh buffer, nucleotides, and common primer(s). Common primers are chosen to provide efficient amplification of the rescued amplicons to provide significant numbers of copies of those amplicons at the end of the second amplification.

By separating the reactions into a first, target-specific primer-driven amplification and a second, target-independent common primer-driven amplification, the inventor has developed a method that will provide specificity through the use of target-specific primers to amplify only the kinds and numbers of nucleic acids present from a particular target, and sensitivity achieved by the use of nested primers, the high concentration of target-specific primers, and the use of the common primer(s) to provide non-specific (target-independent) amplification at higher copy numbers. Furthermore, the use of high-concentration primers in a first amplification, followed by amplicon rescue—particularly when amplicon rescue is performed by isolating a portion of the first amplification by either removing that portion and placing it into a new reaction system or by removing a significant portion of the first amplification and adding to that the necessary reagents to form a second reaction system for a second, target-independent amplification—lends itself to automation. Not only can these steps be performed within a relatively closed reaction system, which limits the possibility of contamination, but the combination of first amplification; amplicon rescue, and second amplification provided by the method produces a specific, sensitive detection method for multiple targets from multiple samples within a period of less than 2 hours.

Target nucleic acids may be isolated from their respective sources by various means known to those of skill in the art. Detection of amplicons produced by the method may also be performed by various means known to those of skill in the art, such as application of the amplicons from the second amplification step to a printed array for hybridization and detection. Common primer sequences may include any sequence that will effectively provide for efficient initiation of an amplification reaction. Such sequences, and methods for designing them, are known to those of skill in the art. The inventor has discovered that primers chosen from among SEQ ID NO: 1 (5'-TTCTTAGCGTATTGGAGTCC-3'), SEQ ID NO:2 (5'-AATGTACAGTATTGCGTTTTG-3'), or a combination of both, provide exceptional results in the second amplification reaction.

The invention also provides primer kits for PCR amplification of target nucleotides, such kits comprising primers chosen from among the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, and combinations thereof.

One example of a method for automation of the method may be provided where the amplifications, separation, and detection are performed using a "lab-on-chip" device in a closed system. For example, a first, target-specific amplification may be performed in a first reaction system (PCR1), where nested, unlabeled, high-concentration target-specific primers may be pre-loaded, together with dNTPs, buffer and enzymes to perform the desired PCR or RT-PCR amplification. After the first amplification has been allowed to proceed for the desired number of cycles, unused primers may be separated from nucleotide amplicons using capillary electrophoresis by means of electrodes activated between the PCR1 (negative) and a waste chamber (positive) to separate the primers from the amplicons. Upon movement of the primers to the waste chamber, the electrode in the waste chamber may be turned off and a second reaction system (PCR2) positively charged. The larger molecular weight amplicons may therefore migrate to the PCR2 chamber, where they are mixed with pre-loaded common primers and fresh enzymes, dNTPs and buffer. After the second amplification is performed in PCR2, the PCR products (amplicons) may be electrophoretically moved to the detection chamber to be hybridized to probes covalently fixed onto beads, the position of the beads in an array representing specific molecular targets. Target detection may therefore be performed by imaging analysis, for example, where positive results may be indicated by bright beads, as amplicons products may be labeled with fluorescent dyes or other chemical/biochemical labels. Unused PCR products and primers may then be removed and deposited in the waste chamber.

In some embodiments, a PCR chip may comprise a first reaction system fluidly connected to both a waste reservoir and a second reaction system, the waste reservoir and second reaction system each additionally comprising at least one electrode, the electrodes comprising a means for separating amplicons produced from the first reaction system. The second reaction system may be fluidly connected to a hybridization and detection chamber, the hybridization and detection chamber comprising microspheres, or beads, arranged so that the physical position of the beads is an indication of a specific target polynucleotide's presence in the sampled analyzed by means of the chip.

The chip may be pre-Loaded with reagents, or the reagents may be added by the user. In one embodiment, pre-loaded reagents may include nested, high-concentration target-specific primers, dNTPs, polymerase enzymes, and buffer(s) for a first reaction system. The second reaction system may be preloaded with common primers, dNTPs, buffer, and polymerase enzymes. Using the chip, for example, a patient sample may be loaded into at least one first reaction system by injecting the sample through soft, rubber-like polydimethylsiloxane (PDMS) material covering all or a portion of the chip. In the first reaction system, the first series of PCR cycles may be performed for the first amplification, to amplify the target sequences and to incorporate common primer binding sequences into at least a portion of the resulting amplicons. Amplicon products from the first reaction system may then be separated by on-chip electrophoresis performed in the microfluidic channel, the first reaction system being fluidly connected to at least one second reaction system and at least one waste reservoir, each of the second reaction systems and waste reservoirs additionally comprising at least one electrode, the electrodes promoting movement of the amplicons and unused primers from the first amplification reaction to a second reaction system and a waste reservoir, respectively. Amplicons moved to a second PCR reaction system may then be then subjected to a second amplification using common primers to amplify amplicons into which at least one common primer binding site has been incorporated during the first amplification in the first reaction system. Following completion of the desired amplification cycles in the second reaction system, the PCR products (amplicons) may be moved by microfluidic electrophoresis from the second reaction system to at least one hybridization and detection chamber, a second reaction system being fluidly connected to at least one hybridization and detection chamber. Within the hybridization and detection chamber may be microspheres, or beads, forming an array, the physical position of the beads indicating the specific target for detection. A bead array may comprise from about 1 to about 200 targets, with each target being represented by from about 1 to about 100 beads. If a specific target is not represented by the appropriate primers in the first amplification reaction, a software mask may be used to cover the related beads so that they will not interfere with the analysis. The hybridization and detection chamber may be fluidly connected to at least one wash chamber and at least one detection chamber, the wash chamber comprising reagents to assist in the removal of unused, labeled, primers and probes to reduce background, and the detection chamber comprising reagents such as streptavidine-Quantum dots, or streptavidine-PE for labeling amplified DNA for imaging analysis.

The method of the invention may also be performed using a standard or modified PCR thermocycler. For example, nucleotides, buffers, and primers may be loaded into standard PCR tubes in a first thermocycler for the first amplification. The contents of the tube may be removed by manual or automated means for rescue of the amplicons, and the newly-isolated amplicons may be placed into a second amplification tube where buffers, nucleotides, and enzyme(s) are introduced in order to perform the second amplification in the first or a second thermocycler, the thermocycler being programmed to cycle the reaction through the appropriate temperatures for the desired lengths of time. It should be understood that cycling times and the number of cycles may vary and may be determined by those of skill in the art.

The use of nested primers appears to improve the binding affinity of the polymerase, producing significantly more amplicons during the first amplification reaction. These amplicons may be produced from a variety of target polynucleotides within the sample, using a high concentration of target-specific primers. By incorporating into at least a portion of the amplicons during the first amplification at least one binding site for at least one common primer, it is then possible, during the second amplification, to even more significantly increase the number of amplicons produced as a result of the amplification process. Common primers are chosen for their binding affinity and capacity to prime amplification during the second amplification. By the use of this three-step method ($1^{st}$ amplification step, amplicon rescue, $2^{nd}$ amplification step), it is therefore possible to increase both the specificity and the sensitivity of the PCR process for identifying one or more target organism(s) from a sample containing multiple organisms. The inventor has discovered that this method does significantly increase both specificity and sensitivity, when compared to previously-described PCR methods.

Automating the amplification-separation-amplification process enables the identification of a significant number of targets within a period of 1-3 hours, and has been shown to be effective for amplifying target nucleic acids from multiple microorganisms within a period of 1.5 hours, allowing rapid identification of a possible causative agent of disease to allow immediate steps to be taken toward treatment, isolation, implementation of public health plans for limiting exposure to epidemic-causing disease agents, bioterror agents, etc.

Samples may be prepared for the PCR reactions by various means known to those of skill in the art. These methods may be provided as instructions provided with PCR kits containing buffers and enzymes, for example, or instructions may be obtained from various journal or patent publications. Methods for handling samples prior to preparation for the PCR amplification steps are also known to those of skill in the art, and may vary depending upon the source of the sample.

Enzymes used for the amplifications are commercially available and may include, for example, Qiagen Multiplex mix or Qiagen Hot Start mix. Buffers are also commercially available, as are nucleotides (dNTPs) and other reagents. Thermocyclers are manufactured by and distributed by a variety of companies including, for example, Applied Biosystems and Bio-Rad. PCR reagent kits may also be obtained from various sources, including, for example, Qiagen (Gaithersburg, Md.).

The invention provides a method that is suitable for identifying a single microorganism or multiple microorganisms, for example, from a sample that may contain a variety of microorganisms. Such a sample may be obtained from a clinical specimen (e.g., blood, saliva, tissue), from an environmental sample (e.g., water, soil), from a food sample, or other source. Microorganisms that may be identified may include various genera and species of bacteria, viruses, and other DNA and/or RNA-containing organisms.

For identification of microorganisms, a method such as the Luminex xMAP® technology may be utilized, and the detection step may be incorporated into the automated system along with the amplifications so that the automated system accomplishes the first amplification, the amplicon rescue, the second amplification, and detection. In the Luminex xMAP® system, for example, microspheres in suspension provide solid support for probe binding, also known as a "liquid chip" or "suspension array." With xMAP® technology, molecular reactions take place on the surface of color-coded microspheres. For each pathogen, target-specific capture probes may be covalently linked to a specific set of color-coded microspheres. Labeled PCR products are captured by the bead-bound capture probes in a hybridization suspension. A microfluidics system delivers the suspension hybridization reaction mixture to a dual-laser detection device. A red laser identifies each bead by its color-coding, while a green laser detects the hybridization signal associated with each bead. Software is used to collect the data and report the results in a matter of seconds. The data is reported in the form of mean fluorescence intensity (MFI).

The method described herein enables one of skill in the art to couple high-specificity, high-sensitivity amplification and detection into one automated system. Using such a system, it is possible to analyze one or more clinical samples in a shorter period of time with greater sensitivity than has previously been possible with existing systems.

The invention may be further described by means of the following non-limiting examples:

Example 1

An arm-PCR reaction was designed to amplify and detect pathogens responsible for food-borne diseases. The target gene used for each pathogen is listed in Table 1 below.

TABLE 1

| Target Organism | Target Gene |
| --- | --- |
| Escherichia coli (E. coli) | rfbE |
| E. coli | eac |
| Salmonella | invA |
| Campylobacter jejuni (1) and coli (2) | ceuE |
| Shigella | ipaH |
| Yersinia enterocolitica | yst |
| Vibrio cholerae | OMPW |
| E. coli (ETEC) heat labile toxin | LT |
| E. coli (STEC) shiga toxin | Stx |
| Vibrio cholerae-cholera toxin | Ctx |
| E. coli (ETEC) heat stable toxin | ST |
| Vibrio parahaemolyticus | tlh |

Primers generated for each target are listed in Table 2. SupF and SupR indicate common primer sequences. Common primer sequences forming the tag for target-specific primers are shown in bold letters. $F_o$, $F_i$, $R_i$ and $R_o$ indicate the nested primers for each amplification target, while the D oligo indicates the detection probe that hybridizes to a specific sequence within the amplicon. The probe is covalently linked to a color coded bead for detection with the Luminex xMAP® instrument.

TABLE 2

| Primer Name | Primer Sequence | SEQ ID NO: |
| --- | --- | --- |
| Sup F | TTCTTAGCGTATTGGAGTCC | 1 |
| Sup R | /5Biosg/AATGTACAGTATTGCGTTTTG | 2 |
| ceuE Fo | CAACAAGTTGATTTTGAAGC | 3 |
| ceuE Fi | TTCTTAGCGTATTGGAGTCCATTAATGCTTTAAAACCTGATC | 4 |
| ceuE Ri | AATGTACAGTATTGCGTTTTGTTAAAAAATTTGCATTATCAAG | 5 |
| ceue Ro | ACCATAAAGTTTTGCAACGC | 6 |

TABLE 2-continued

| Primer Name | Primer Sequence | SEQ ID NO: |
|---|---|---|
| ceuE D1 | /5AmMC12/CTC CAA CTT TAT TTG TAG | 7 |
| ceuE2 Fo | CAACAAGTTGATTTTGAAGC | 8 |
| ceuE2 Fi | TTCTTAGCGTATTGGAGTCCATTAATGCTTTAAAACCTGATC | 9 |
| ceuE2 Ri | AATGTACAGTATTGCGTTTTGTTAAAAAATTTGCATTATCAAG | 10 |
| ceuE2 Ro | ACCATAAAGTTTTGCAACGC | 11 |
| ceuE D2 | /5AmMC12/CTC CAA CTA TGT TTG TAG | 12 |
| rfbE2 Fo | AGGATTAGCTGTACATAGGC | 13 |
| rfbE2 Fi | TTCTTAGCGTATTGGAGTCCGGCATGACGTTATAGGCTAC | 14 |
| rfbE2 Ri | AATGTACAGTATTGCGTTTTGTGTTCTAACTGGGCTAATCC | 15 |
| rfbE2 Ro | CGTGATATAAAATCATCAGC | 16 |
| rfbE2 D | /5AmMC12/GACAAATATCTGCGCTGCTAT | 17 |
| eac1 Fo | CGATTACGCGAAAGATACCG | 18 |
| eac1 Fi | TTCTTAGCGTATTGGAGTCCCAGGCTTCGTCACAGTTGC | 19 |
| eac1 Ri | AATGTACAGTATTGCGTTTTGCCAGTGAACTACCGTCAAAG | 20 |
| eac1 Ro | TTTTCGGAATCATAGAACGG | 21 |
| eac1 D | /5AmMC12/TTATGGAACGGCAGAGGTTA | 22 |
| invA1 Fo | AACAGTGCTCGTTTACGACC | 23 |
| invA1 Fi | TTCTTAGCGTATTGGAGTCCTGGTACTAATGGTGATGATC | 24 |
| invA1 Ri | AATGTACAGTATTGCGTTTTGGCGATCAGGAAATCAACCAG | 25 |
| invA1 Ro | TGTAGAACGACCCCATAAAC | 26 |
| invA1 D | /5AmMC12/TCGTCATTCCATTACCTACC | 27 |
| ipaH2 Fo | GGATTCCGTGAACAGGTCGC | 28 |
| ipa H2 Fi | TTCTTAGCGTATTGGAGTCCGCATGGCTGGAAAAACTCAG | 29 |
| ipa H2 Ri | AATGTACAGTATTGCGTTTTGTCAGTGGCATCAGCAGCAAC | 30 |
| ipaH 2 Ro | CGCGACACGGTCCTCACAGC | 31 |
| ipa H2 D | /5AmMC12/AGCTTCGACAGCAGTCTTTC | 32 |
| yst Fo | GAAAAAGATAGTTTTTGTTC | 33 |
| yst Fi | TTCTTAGCGTATTGGAGTCCATGCTGTCTTCATTTGGAGC | 34 |
| yst Ri | AATGTACAGTATTGCGTTTTGGTGTCGATAATGCATCACTG | 35 |
| yst Ro | CTTGTATACCTCAGCGGTTA | 36 |
| yst D | /5AmMC12/CGGCCAAGAAACAGTTTCAG | 37 |
| ompW Fo | CAAGTTTGTGTGATTTTGTG | 38 |
| ompW Fi | TTCTTAGCGTATTGGAGTCCCACAAAGATAACAACATAGCCC | 39 |
| ompW Ri | AATGTACAGTATTGCGTTTTGTACGGCTAGGCAAATGGTTT | 40 |
| ompW Ro | GTGAGCAAATACAGGAGCGG | 41 |
| ompW D1 | /5AmMC12/AGGAAAACGTCATGAAAC | 42 |
| ompW2 Fo | GTGAGTTGGCAGTTAATAGC | 43 |
| ompW2 Fi | TTCTTAGCGTATTGGAGTCCGGTTAACGCTTGGCTATATG | 44 |
| ompW2 Ri | AATGTACAGTATTGCGTTTTGGTAGAAATCTTATGTGAAAA | 45 |

TABLE 2-continued

| Primer Name | Primer Sequence | SEQ ID NO: |
|---|---|---|
| ompW2 Ro | CTACCTAACTCACCACCAGA | 46 |
| ompW D2 | /5AmMC12/CTGACAACATCAGTTTTG | 47 |
| LT1 Fo | TCGATAGAGGAACTCAAATG | 48 |
| LT1 Fi | TTCTTAGCGTATTGGAGTCCTCTTTATGATCACGCGAGAG | 49 |
| LT1 Ri | AATGTACAGTATTGCGTTTTGAAACATATCCGTCATCATA | 50 |
| LT1 Ro | CTTCTCAAACTAAGAGAAGT | 51 |
| LT1 D | /5AmMC12/GAACACAAACCGGCTTT | 52 |
| LT2 Fo | TATGTTTAATGTTAATGATG | 53 |
| LT2 Fi | TTCTTAGCGTATTGGAGTCCATACAGCCCTCACCCATATG | 54 |
| LT2 Ri | AATGTACAGTATTGCGTTTTGCTGAGAATATGGTATTCCAC | 55 |
| LT2 Ro | CCAAAATTAACACGATACCA | 56 |
| LT2 D | /5AmMC12/AGGAGGTTTCTGCGTTA | 57 |
| stx Fo | CATATATCTCAGGGGACCAC | 58 |
| stx Fi | TTCTTAGCGTATTGGAGTCCGTGTCTGTTATTAACCACAC | 59 |
| stx Ri | AATGTACAGTATTGCGTTTTGGTCAAACGCGCCTGATAGA | 60 |
| stx Ro | TTATTTTGCTCAATAATCAG | 61 |
| stx D | /5AmMC12/GGGCAGTTATTTTGCTG | 62 |
| stx2 Fo | ACAACGGTTTCCATGACAAC | 63 |
| stx2 Fi | TTCTTAGCGTATTGGAGTCCGGACAGCAGTTATACCACTC | 64 |
| stx2 Ri | AATGTACAGTATTGCGTTTTGGAAACCAGTGAGTGACGACT | 65 |
| stx2 Ro | CCATTAACGCCAGATATGAT | 66 |
| stx2 D | /5AmMC12/ACGTTCCGGAATGCAAAT | 67 |
| ctx1 Fo | CAGATTCTAGACCTCCTGATG | 68 |
| ctx1 Fi | TTCTTAGCGTATTGGAGTCCAGCAGTCAGGTGGTCTTATG | 69 |
| ctx1 Ri | AATGTACAGTATTGCGTTTTGCATTTGAGTACCTCGGTCAA | 70 |
| ctx1 Ro | CTTGCATGATCATAAAGGTTG | 71 |
| ctx1 D | /5AmMC12/AGAGGACAGAGTGAGTAC | 72 |
| ctx2 Fo | GGGCTACAGAGATAGATATTAC | 73 |
| ctx2 Fi | TTCTTAGCGTATTGGAGTCCAGATATTGCTCCAGCAGCAG | 74 |
| ctx2 Ri | AATGTACAGTATTGCGTTTTGCATGATGAATCCACGGCTCT | 75 |
| ctx2 Ro | CGATGATCTTGGAGCATTCC | 76 |
| ctx2 D | /5AmMC12/TATGGATTGGCAGGTTTC | 77 |
| ST Fo | CTTTTTCACCTTTCGCTCAG | 78 |
| ST Fi | TTCTTAGCGTATTGGAGTCCGATGCTAAACCAGCAGGGTC | 79 |
| ST Ri | AATGTACAGTATTGCGTTTTGCAATTCACAGCAGTAATTGC | 80 |
| ST Ro | CCGGTACAAGCAGGATTACA | 81 |
| ST D | /5AmMC12/AGTAGTCCTGAAAGCATG | 82 |
| tlh1 Fo | GATTCGTTTGACGGACGCAG | 83 |
| tlh1 Fi | TTCTTAGCGTATTGGAGTCCCATGTTGATGACACTGCCAG | 84 |

TABLE 2-continued

| Primer Name | Primer Sequence | SEQ ID NO: |
|---|---|---|
| tlh1 Ri | AATGTACAGTATTGCGTTTTGCGATCTCTTCTTGTGTTGAG | 85 |
| tlh1 Ro | CAAGCACTTTCGCACGAATT | 86 |
| tlh1 D | /5AmMC12/AAAGCGCCTCAGTTTAAG | 87 |
| tlh2 Fo | AAGAGCACGGTTTCGTGAAC | 88 |
| tlh2 Fi | TTCTTAGCGTATTGGAGTCCGACATCAACCGCTCATCGTC | 89 |
| tlh2 Ri | AATGTACAGTATTGCGTTTTGCAGAACACAAACTTCTCAGC | 90 |
| tlh2 Ro | CGGTGAGTTGCTGTTGTTGG | 91 |
| tlh2 D | /5AmMC12/ATGTACACCCACGCATTG | 92 |

A primer mix containing 10 pmol of each of the $F_o$, $F_i$, $R_i$ and $R_o$ primers in Table 2. For this amplification, only one target template, Campylobacter jejuni, was included. The template was diluted to 10 pg/μl, 1 pg/μl, 0.1 pg/μl, 0.01 pg/μl, and 0.001 pg/μl. A Qiagen Multiplex PCR kit was used to prepare a sample containing 44 μl of Multiplex Mix, 5 μl of primer mix, and 1 μl of template. Cycling conditions were as follows:

95° C. for 15 minutes
94° C. for 15 seconds
55° C. for 15 seconds
72° C. for 15 seconds
These three cycles repeated, 2-20 times (15 times total for this example.)
94° C. for 15 seconds
70° C. for 15 seconds
These two cycles repeated, 6 times total for this example.
72° C. for 3 minutes
4° C. hold Upon completion of the first amplification as described above, samples were added to Millipore columns with a molecular weight cut-off of 50 kd and spun for 11 minutes at 13 k RPM to remove a substantial portion of the primers (molecular weight generally below 30 kd), rescuing amplicons with a molecular weight generally above 70 kd on top of the filter. The column was flipped and spun in a new collection tube for approximately 30 seconds to recover the amplicon for the next round of amplification.

10 μl of sample from the collection tube was added to is 15 μl of Multiplex Mix, 1 μl of common primers, 10 pmol for the forward common primer and 40 pmol for the reverse common primer, and 14 μl of H₂O. Samples were then placed in a thermocycler (Applied Biosystems, Foster City, Calif.) and run through the following cycles:

95° C. for 15 minutes (to heat activate the enzyme)
94° C. for 15 seconds
55° C. for 15 seconds×30 cycles
72° C. for 15 seconds
72° C. for 3 minutes
4° C. hold Hybridization was performed using 5 μl of PCR product added to 35 μl of bead (microsphere) mix and allowed to hybridize at 52° C. for 10 minutes. After 10 minutes, 10 μl of SA-PE was added (2× SA-PE, Genaco Biomedical Sciences, Inc., was diluted 1:2 with 1×TMAC) to each sample and allowed to hybridize at 52° C. for 5 minutes. After 5 minutes, 120 μl of 52° C. stop buffer was added to each sample and the samples were analyzed using a Luminex200 machine.

Mean fluorescence intensity (MFI) numbers for arm-PCR and tem-PCR reactions are shown in Table 3.

TABLE 3

| Template Concentration | High concentration nested primers - MFI | Low concentration nested primers - MFI |
|---|---|---|
| 10 pg/μl | 693 | 999 |
| 1 pg/μl | 575 | 633 |
| 0.1 pg/μl | 573 | 281 |
| 0.01 pg/μl | 430 | 126 |
| 0.001 pg/μl | 298 | 68 |
| Blank | 64 | 59 |

These results indicate that although the signal is higher at high template concentrations when low concentration nested primers are used, the sensitivity of the high concentration nested primer method is about two logs higher. If the positive signal cutoff is 250 MFI, for example, this method can detect as little as 0.001 pg/μl, while the results of method previously described in the art for low concentration nested primers are negative between 0.1 pg/μl and 0.01 pg/μl. The time required for the entire process is approximately 210 minutes when using low concentration nested primers and approximately 150 minutes when using high concentration nested primers.

What is claimed is:

1. A primer kit comprising: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, and SEQ ID NO: 92.

\* \* \* \* \*

SEQUENCE LISTING

<160> NUMBER OF SEQ ID NOS: 92

<210> SEQ ID NO 1
<211> LENGTH: 20
<212> TYPE: DNA
<213> ORGANISM: Artificial Sequence
<220> FEATURE:
<223> OTHER INFORMATION: Primer

```
<220> FEATURE:
<221> NAME/KEY: primer_bind
<222> LOCATION: (1)..(20)

<400> SEQUENCE: 1
ttcttagcgt attggagtcc                                                    20

<210> SEQ ID NO 2
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(21)

<400> SEQUENCE: 2
aatgtacagt attgcgtttt g                                                  21

<210> SEQ ID NO 3
<211> LENGTH: 20
<212> TYPE: DNA
<213> ORGANISM: Campylobacter jejuni
<220> FEATURE:
<221> NAME/KEY: primer_bind
<222> LOCATION: (1)..(20)

<400> SEQUENCE: 3
caacaagttg attttgaagc                                                    20

<210> SEQ ID NO 4
<211> LENGTH: 42
<212> TYPE: DNA
<213> ORGANISM: Campylobacter jejuni
<220> FEATURE:
<221> NAME/KEY: primer_bind
<222> LOCATION: (1)..(42)

<400> SEQUENCE: 4
ttcttagcgt attggagtcc attaatgctt taaaacctga tc                           42

<210> SEQ ID NO 5
<211> LENGTH: 43
<212> TYPE: DNA
<213> ORGANISM: Campylobacter jejuni
<220> FEATURE:
<221> NAME/KEY: prim_bind
<222> LOCATION: (1)..(43)

<400> SEQUENCE: 5
aatgtacagt attgcgtttt gttaaaaaat ttgcattatc aag                          43

<210> SEQ ID NO 6
<211> LENGTH: 20
<212> TYPE: DNA
<213> ORGANISM: Campylobacter jejuni
<220> FEATURE:
<221> NAME/KEY: prim_bind
<222> LOCATION: (1)..(20)

<400> SEQUENCE: 6
accataaagt tttgcaacgc                                                    20

<210> SEQ ID NO 7
<211> LENGTH: 18
<212> TYPE: DNA
<213> ORGANISM: Campylobacter jejuni
```

```
<220> FEATURE:
<221> NAME/KEY: primer_bind
<222> LOCATION: (1)..(18)

<400> SEQUENCE: 7 ctccaactttatttgtag                                                        18

<210> SEQ ID NO 8
<211> LENGTH: 20
<212> TYPE: DNA
<213> ORGANISM: Campylobacter coli
<220> FEATURE:
<221> NAME/KEY: primer_bind
<222> LOCATION: (1)..(20)

<400> SEQUENCE: 8
caacaagttg attttgaagc                                                     20

<210> SEQ ID NO 9
<211> LENGTH: 42
<212> TYPE: DNA
<213> ORGANISM: Campylobacter coli
<220> FEATURE:
<221> NAME/KEY: primer_bind
<222> LOCATION: (1)..(42)

<400> SEQUENCE: 9
ttcttagcgt attggagtcc attaatgctt taaaacctga tc                            42

<210> SEQ ID NO 10
<211> LENGTH: 43
<212> TYPE: DNA
<213> ORGANISM: Campylobacter coli
<220> FEATURE:
<221> NAME/KEY: primer_bind
<222> LOCATION: (1)..(43)

<400> SEQUENCE: 10
aatgtacagt attgcgtttt gttaaaaaat ttgcattatc aag                           43

<210> SEQ ID NO 11
<211> LENGTH: 20
<212> TYPE: DNA
<213> ORGANISM: Campylobacter coli
<220> FEATURE:
<221> NAME/KEY: primer_bind
<222> LOCATION: (1)..(20)

<400> SEQUENCE: 11
accataaagt tttgcaacgc                                                     20

<210> SEQ ID NO 12
<211> LENGTH: 18
<212> TYPE: DNA
<213> ORGANISM: Campylobacter coli
<220> FEATURE:
<221> NAME/KEY: primer_bind
<222> LOCATION: (1)..(18)

<400> SEQUENCE: 12
ctccaactat gtttgtag                                                       18

<210> SEQ ID NO 13
<211> LENGTH: 20
<212> TYPE: DNA
<213> ORGANISM: Escherichia coli
<220> FEATURE:
<221> NAME/KEY: prim_bind
```

```
<222> LOCATION: (1)..(20)

<400> SEQUENCE: 13
aggattagct gtacataggc                                                    20

<210> SEQ ID NO 14
<211> LENGTH: 40
<212> TYPE: DNA
<213> ORGANISM: Escherichia coli
<220> FEATURE:
<221> NAME/KEY: prim_bind
<222> LOCATION: (1)..(40)

<400> SEQUENCE: 14
ttcttagcgt attggagtcc ggcatgacgt tataggctac                              40

<210> SEQ ID NO 15
<211> LENGTH: 41
<212> TYPE: DNA
<213> ORGANISM: Escherichia coli
<220> FEATURE:
<221> NAME/KEY: prim_bind
<222> LOCATION: (1)..(41)

<400> SEQUENCE: 15
aatgtacagt attgcgtttt gtgttctaac tgggctaatc c                            41

<210> SEQ ID NO 16
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 16
cgtgatataa aatcatcagc                                                    20

<210> SEQ ID NO 17
<211> LENGTH: 21
<212> TYPE: DNA
<213> ORGANISM: Escherichia coli
<220> FEATURE:
<221> NAME/KEY: prim_bind
<222> LOCATION: (1)..(21)

<400> SEQUENCE: 17
gacaaatatc tgcgctgcta t                                                  21

<210> SEQ ID NO 18
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 18
cgattacgcg aaagataccg                                                    20

<210> SEQ ID NO 19
<211> LENGTH: 40
<212> TYPE: DNA
<213> ORGANISM: Escherichia coli
<220> FEATURE:
<221> NAME/KEY: prim_bind
<222> LOCATION: (1)..(40)
```

```
<400> SEQUENCE: 19
ttcttagcgt attggagtcc ccaggcttcg tcacagttgc                          40

<210> SEQ ID NO 20
<211> LENGTH: 41
<212> TYPE: DNA
<213> ORGANISM: Escherichia coli
<220> FEATURE:
<221> NAME/KEY: prim_bind
<222> LOCATION: (1)..(41)

<400> SEQUENCE: 20
aatgtacagt attgcgtttt gccagtgaac taccgtcaaa g                        41

<210> SEQ ID NO 21
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 21
ttttcggaat catagaacgg                                                20

<210> SEQ ID NO 22
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 22
ttatggaacg gcagaggtta                                                20

<210> SEQ ID NO 23
<211> LENGTH: 20
<212> TYPE: DNA
<213> ORGANISM: Salmonella typhimurium
<220> FEATURE:
<221> NAME/KEY: prim_bind
<222> LOCATION: (1)..(20)

<400> SEQUENCE: 23
aacagtgctc gtttacgacc                                                20

<210> SEQ ID NO 24
<211> LENGTH: 41
<212> TYPE: DNA
<213> ORGANISM: Salmonella typhimurium
<220> FEATURE:
<221> NAME/KEY: prim_bind
<222> LOCATION: (1)..(41)

<400> SEQUENCE: 24
ttcttagcgt attggagtcc ctggtactaa tggtgatgat c                        41

<210> SEQ ID NO 25
<211> LENGTH: 41
<212> TYPE: DNA
<213> ORGANISM: Salmonella typhimurium
<220> FEATURE:
<221> NAME/KEY: prim_bind
<222> LOCATION: (1)..(41)

<400> SEQUENCE: 25
```

```
aatgtacagt attgcgtttt ggcgatcagg aaatcaacca g          41

<210> SEQ ID NO 26
<211> LENGTH: 20
<212> TYPE: DNA
<213> ORGANISM: Salmonella typhimurium
<220> FEATURE:
<221> NAME/KEY: prim_bind
<222> LOCATION: (1)..(20)

<400> SEQUENCE: 26
tgtagaacga ccccataaac                                   20

<210> SEQ ID NO 27
<211> LENGTH: 20
<212> TYPE: DNA
<213> ORGANISM: Salmonella typhimurium
<220> FEATURE:
<221> NAME/KEY: prim_bind
<222> LOCATION: (1)..(20)

<400> SEQUENCE: 27
tcgtcattcc attacctacc                                   20

<210> SEQ ID NO 28
<211> LENGTH: 20
<212> TYPE: DNA
<213> ORGANISM: Shigella flexneri
<220> FEATURE:
<221> NAME/KEY: prim_bind
<222> LOCATION: (1)..(20)

<400> SEQUENCE: 28
ggattccgtg aacaggtcgc                                   20

<210> SEQ ID NO 29
<211> LENGTH: 40
<212> TYPE: DNA
<213> ORGANISM: Shigella flexneri
<220> FEATURE:
<221> NAME/KEY: prim_bind
<222> LOCATION: (1)..(40)

<400> SEQUENCE: 29
ttcttagcgt attggagtcc gcatggctgg aaaaactcag             40

<210> SEQ ID NO 30
<211> LENGTH: 41
<212> TYPE: DNA
<213> ORGANISM: Shigella flexneri
<220> FEATURE:
<221> NAME/KEY: prim_bind
<222> LOCATION: (1)..(41)

<400> SEQUENCE: 30
aatgtacagt attgcgtttt gtcagtggca tcagcagcaa c           41

<210> SEQ ID NO 31
<211> LENGTH: 20
<212> TYPE: DNA
<213> ORGANISM: Shigella flexneri
<220> FEATURE:
<221> NAME/KEY: prim_bind
<222> LOCATION: (1)..(20)

<400> SEQUENCE: 31
cgcgacacgg tcctcacagc                                   20
```

```
<210> SEQ ID NO 32
<211> LENGTH: 20
<212> TYPE: DNA
<213> ORGANISM: Shigella flexneri
<220> FEATURE:
<221> NAME/KEY: prim_bind
<222> LOCATION: (1)..(20)

<400> SEQUENCE: 32
agcttcgaca gcagtctttc                                              20

<210> SEQ ID NO 33
<211> LENGTH: 20
<212> TYPE: DNA
<213> ORGANISM: Yersinia enterocolitica
<220> FEATURE:
<221> NAME/KEY: prim_bind
<222> LOCATION: (1)..(20)

<400> SEQUENCE: 33
gaaaaagata gttttttgttc                                             20

<210> SEQ ID NO 34
<211> LENGTH: 40
<212> TYPE: DNA
<213> ORGANISM: Yersinia enterocolitica
<220> FEATURE:
<221> NAME/KEY: prim_bind
<222> LOCATION: (1)..(40)

<400> SEQUENCE: 34
ttcttagcgt attggagtcc atgctgtctt catttggagc                        40

<210> SEQ ID NO 35
<211> LENGTH: 41
<212> TYPE: DNA
<213> ORGANISM: Yersinia enterocolitica
<220> FEATURE:
<221> NAME/KEY: prim_bind
<222> LOCATION: (1)..(41)

<400> SEQUENCE: 35
aatgtacagt attgcgtttt ggtgtcgata atgcatcact g                      41

<210> SEQ ID NO 36
<211> LENGTH: 20
<212> TYPE: DNA
<213> ORGANISM: Yersinia enterocolitica
<220> FEATURE:
<221> NAME/KEY: prim_bind
<222> LOCATION: (1)..(20)

<400> SEQUENCE: 36
cttgtatacc tcagcggtta                                              20

<210> SEQ ID NO 37
<211> LENGTH: 20
<212> TYPE: DNA
<213> ORGANISM: Yersinia enterocolitica
<220> FEATURE:
<221> NAME/KEY: prim_bind
<222> LOCATION: (1)..(20)

<400> SEQUENCE: 37
cggccaagaa acagtttcag                                              20

<210> SEQ ID NO 38
```

```
<211> LENGTH: 21
<212> TYPE: DNA
<213> ORGANISM: Vibrio cholerae
<220> FEATURE:
<221> NAME/KEY: prim_bind
<222> LOCATION: (1)..(21)

<400> SEQUENCE: 38
caagtttgtg tgattttttgt g                                              21

<210> SEQ ID NO 39
<211> LENGTH: 42
<212> TYPE: DNA
<213> ORGANISM: Vibrio cholerae
<220> FEATURE:
<221> NAME/KEY: prim_bind
<222> LOCATION: (1)..(42)

<400> SEQUENCE: 39
ttcttagcgt attggagtcc cacaaagata acaacatagc cc                        42

<210> SEQ ID NO 40
<211> LENGTH: 41
<212> TYPE: DNA
<213> ORGANISM: Vibrio cholerae
<220> FEATURE:
<221> NAME/KEY: prim_bind
<222> LOCATION: (1)..(41)

<400> SEQUENCE: 40
aatgtacagt attgcgtttt gtacggctag gcaaatggtt t                         41

<210> SEQ ID NO 41
<211> LENGTH: 20
<212> TYPE: DNA
<213> ORGANISM: Vibrio cholerae
<220> FEATURE:
<221> NAME/KEY: prim_bind
<222> LOCATION: (1)..(20)

<400> SEQUENCE: 41
gtgagcaaat acaggagcgg                                                 20

<210> SEQ ID NO 42
<211> LENGTH: 18
<212> TYPE: DNA
<213> ORGANISM: Vibrio cholerae
<220> FEATURE:
<221> NAME/KEY: prim_bind
<222> LOCATION: (1)..(18)

<400> SEQUENCE: 42
aggaaaacgt catgaaac                                                   18

<210> SEQ ID NO 43
<211> LENGTH: 20
<212> TYPE: DNA
<213> ORGANISM: Vibrio cholerae
<220> FEATURE:
<221> NAME/KEY: prim_bind
<222> LOCATION: (1)..(20)

<400> SEQUENCE: 43
gtgagttggc agttaatagc                                                 20

<210> SEQ ID NO 44
<211> LENGTH: 40
<212> TYPE: DNA
```

```
<213> ORGANISM: Vibrio cholerae
<220> FEATURE:
<221> NAME/KEY: prim_bind
<222> LOCATION: (1)..(40)

<400> SEQUENCE: 44
ttcttagcgt attggagtcc ggttaacgct tggctatatg                              40

<210> SEQ ID NO 45
<211> LENGTH: 41
<212> TYPE: DNA
<213> ORGANISM: Vibrio cholerae
<220> FEATURE:
<221> NAME/KEY: prim_bind
<222> LOCATION: (1)..(41)

<400> SEQUENCE: 45
aatgtacagt attgcgtttt ggtagaaatc ttatgtgaaa a                            41

<210> SEQ ID NO 46
<211> LENGTH: 20
<212> TYPE: DNA
<213> ORGANISM: Vibrio cholerae
<220> FEATURE:
<221> NAME/KEY: prim_bind
<222> LOCATION: (1)..(20)

<400> SEQUENCE: 46
ctacctaact caccaccaga                                                    20

<210> SEQ ID NO 47
<211> LENGTH: 18
<212> TYPE: DNA
<213> ORGANISM: Vibrio cholerae
<220> FEATURE:
<221> NAME/KEY: prim_bind
<222> LOCATION: (1)..(18)

<400> SEQUENCE: 47
ctgacaacat cagttttg                                                      18

<210> SEQ ID NO 48
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 48
tcgatagagg aactcaaatg                                                    20

<210> SEQ ID NO 49
<211> LENGTH: 40
<212> TYPE: DNA
<213> ORGANISM: Escherichia coli
<220> FEATURE:
<221> NAME/KEY: prim_bind
<222> LOCATION: (1)..(40)

<400> SEQUENCE: 49
ttcttagcgt attggagtcc tctttatgat cacgcgagag                              40

<210> SEQ ID NO 50
<211> LENGTH: 41
<212> TYPE: DNA
<213> ORGANISM: Escherichia coli
<220> FEATURE:
```

```
<221> NAME/KEY: prim_bind
<222> LOCATION: (1)..(41)

<400> SEQUENCE: 50
aatgtacagt attgcgtttt ggaaacatat ccgtcatcat a                41

<210> SEQ ID NO 51
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 51
cttctcaaac taagagaagt                                        20

<210> SEQ ID NO 52
<211> LENGTH: 17
<212> TYPE: DNA
<213> ORGANISM: Escherichia coli
<220> FEATURE:
<221> NAME/KEY: prim_bind
<222> LOCATION: (1)..(17)

<400> SEQUENCE: 52
gaacacaaac cggcttt                                           17

<210> SEQ ID NO 53
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 53
tatgtttaat gttaatgatg                                        20

<210> SEQ ID NO 54
<211> LENGTH: 40
<212> TYPE: DNA
<213> ORGANISM: Escherichia coli
<220> FEATURE:
<221> NAME/KEY: prim_bind
<222> LOCATION: (1)..(40)

<400> SEQUENCE: 54
ttcttagcgt attggagtcc atacagccct cacccatatg                  40

<210> SEQ ID NO 55
<211> LENGTH: 41
<212> TYPE: DNA
<213> ORGANISM: Escherichia coli
<220> FEATURE:
<221> NAME/KEY: prim_bind
<222> LOCATION: (1)..(41)

<400> SEQUENCE: 55
aatgtacagt attgcgtttt gctgagaata tggtattcca c                41

<210> SEQ ID NO 56
<211> LENGTH: 20
<212> TYPE: DNA
<213> ORGANISM: Escherichia coli
<220> FEATURE:
<221> NAME/KEY: prim_bind
<222> LOCATION: (1)..(20)
```

```
<400> SEQUENCE: 56
ccaaaattaa cacgatacca                                              20

<210> SEQ ID NO 57
<211> LENGTH: 17
<212> TYPE: DNA
<213> ORGANISM: Escherichia coli
<220> FEATURE:
<221> NAME/KEY: prim_bind
<222> LOCATION: (1)..(17)

<400> SEQUENCE: 57
aggaggtttc tgcgtta                                                 17

<210> SEQ ID NO 58
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 58
catatatctc aggggaccac                                              20

<210> SEQ ID NO 59
<211> LENGTH: 40
<212> TYPE: DNA
<213> ORGANISM: Escherichia coli
<220> FEATURE:
<221> NAME/KEY: prim_bind
<222> LOCATION: (1)..(40)

<400> SEQUENCE: 59
ttcttagcgt attggagtcc gtgtctgtta ttaaccacac                        40

<210> SEQ ID NO 60
<211> LENGTH: 41
<212> TYPE: DNA
<213> ORGANISM: Escherichia coli
<220> FEATURE:
<221> NAME/KEY: prim_bind
<222> LOCATION: (1)..(41)

<400> SEQUENCE: 60
aatgtacagt attgcgtttt ggtcaaaacg cgcctgatag a                      41

<210> SEQ ID NO 61
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 61
ttattttgct caataatcag                                              20

<210> SEQ ID NO 62
<211> LENGTH: 17
<212> TYPE: DNA
<213> ORGANISM: Escherichia coli
<220> FEATURE:
<221> NAME/KEY: prim_bind
<222> LOCATION: (1)..(17)

<400> SEQUENCE: 62
```

```
gggcagttat tttgctg                                                    17
```

<210> SEQ ID NO 63
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 63

```
acaacggttt ccatgacaac                                                 20
```

<210> SEQ ID NO 64
<211> LENGTH: 40
<212> TYPE: DNA
<213> ORGANISM: Escherichia coli
<220> FEATURE:
<221> NAME/KEY: prim_bind
<222> LOCATION: (1)..(40)

<400> SEQUENCE: 64

```
ttcttagcgt attggagtcc ggacagcagt tataccactc                           40
```

<210> SEQ ID NO 65
<211> LENGTH: 41
<212> TYPE: DNA
<213> ORGANISM: Escherichia coli
<220> FEATURE:
<221> NAME/KEY: prim_bind
<222> LOCATION: (1)..(41)

<400> SEQUENCE: 65

```
aatgtacagt attgcgtttt ggaaaccagt gagtgacgac t                         41
```

<210> SEQ ID NO 66
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 66

```
ccattaacgc cagatatgat                                                 20
```

<210> SEQ ID NO 67
<211> LENGTH: 18
<212> TYPE: DNA
<213> ORGANISM: Escherichia coli
<220> FEATURE:
<221> NAME/KEY: prim_bind
<222> LOCATION: (1)..(18)

<400> SEQUENCE: 67

```
acgttccgga atgcaaat                                                   18
```

<210> SEQ ID NO 68
<211> LENGTH: 21
<212> TYPE: DNA
<213> ORGANISM: Vibrio cholerae
<220> FEATURE:
<221> NAME/KEY: prim_bind
<222> LOCATION: (1)..(21)

<400> SEQUENCE: 68

```
cagattctag acctcctgat g                                               21
```

<210> SEQ ID NO 69
<211> LENGTH: 40
<212> TYPE: DNA
<213> ORGANISM: Vibrio cholerae
<220> FEATURE:
<221> NAME/KEY: prim_bind
<222> LOCATION: (1)..(40)

<400> SEQUENCE: 69
ttcttagcgt attggagtcc agcagtcagg tggtcttatg                40

<210> SEQ ID NO 70
<211> LENGTH: 41
<212> TYPE: DNA
<213> ORGANISM: Vibrio cholerae
<220> FEATURE:
<221> NAME/KEY: prim_bind
<222> LOCATION: (1)..(41)

<400> SEQUENCE: 70
aatgtacagt attgcgtttt gcatttgagt acctcggtca a             41

<210> SEQ ID NO 71
<211> LENGTH: 21
<212> TYPE: DNA
<213> ORGANISM: Vibrio cholerae
<220> FEATURE:
<221> NAME/KEY: prim_bind
<222> LOCATION: (1)..(21)

<400> SEQUENCE: 71
cttgcatgat cataaaggtt g                                   21

<210> SEQ ID NO 72
<211> LENGTH: 18
<212> TYPE: DNA
<213> ORGANISM: Vibrio cholerae
<220> FEATURE:
<221> NAME/KEY: prim_bind
<222> LOCATION: (1)..(18)

<400> SEQUENCE: 72
agaggacaga gtgagtac                                       18

<210> SEQ ID NO 73
<211> LENGTH: 22
<212> TYPE: DNA
<213> ORGANISM: Vibrio cholerae
<220> FEATURE:
<221> NAME/KEY: prim_bind
<222> LOCATION: (1)..(22)

<400> SEQUENCE: 73
gggctacaga gatagatatt ac                                  22

<210> SEQ ID NO 74
<211> LENGTH: 40
<212> TYPE: DNA
<213> ORGANISM: Vibrio cholerae
<220> FEATURE:
<221> NAME/KEY: prim_bind
<222> LOCATION: (1)..(40)

<400> SEQUENCE: 74
ttcttagcgt attggagtcc agatattgct ccagcagcag                40

```
<210> SEQ ID NO 75
<211> LENGTH: 41
<212> TYPE: DNA
<213> ORGANISM: Vibrio cholerae
<220> FEATURE:
<221> NAME/KEY: prim_bind
<222> LOCATION: (1)..(41)

<400> SEQUENCE: 75
aatgtacagt attgcgtttt gcatgatgaa tccacggctc t          41

<210> SEQ ID NO 76
<211> LENGTH: 20
<212> TYPE: DNA
<213> ORGANISM: Vibrio cholerae
<220> FEATURE:
<221> NAME/KEY: prim_bind
<222> LOCATION: (1)..(20)

<400> SEQUENCE: 76
cgatgatctt ggagcattcc                                  20

<210> SEQ ID NO 77
<211> LENGTH: 18
<212> TYPE: DNA
<213> ORGANISM: Vibrio cholerae
<220> FEATURE:
<221> NAME/KEY: prim_bind
<222> LOCATION: (1)..(18)

<400> SEQUENCE: 77
tatggattgg caggtttc                                    18

<210> SEQ ID NO 78
<211> LENGTH: 20
<212> TYPE: DNA
<213> ORGANISM: Escherichia coli
<220> FEATURE:
<221> NAME/KEY: prim_bind
<222> LOCATION: (1)..(20)

<400> SEQUENCE: 78 cttttttcacc tttcgctcag                                 20

<210> SEQ ID NO 79
<211> LENGTH: 40
<212> TYPE: DNA
<213> ORGANISM: Escherichia coli
<220> FEATURE:
<221> NAME/KEY: prim_bind
<222> LOCATION: (1)..(40)

<400> SEQUENCE: 79
ttcttagcgt attggagtcc gatgctaaac cagcagggtc            40

<210> SEQ ID NO 80
<211> LENGTH: 41
<212> TYPE: DNA
<213> ORGANISM: Escherichia coli
<220> FEATURE:
<221> NAME/KEY: prim_bind
<222> LOCATION: (1)..(41)

<400> SEQUENCE: 80
aatgtacagt attgcgtttt gcaattcaca gcagtaattg c          41

<210> SEQ ID NO 81
<211> LENGTH: 20
```

```
<212> TYPE: DNA
<213> ORGANISM: Escherichia coli
<220> FEATURE:
<221> NAME/KEY: prim_bind
<222> LOCATION: (1)..(20)

<400> SEQUENCE: 81
ccggtacaag caggattaca                                                  20

<210> SEQ ID NO 82
<211> LENGTH: 18
<212> TYPE: DNA
<213> ORGANISM: Escherichia coli
<220> FEATURE:
<221> NAME/KEY: prim_bind
<222> LOCATION: (1)..(18)

<400> SEQUENCE: 82
agtagtcctg aaagcatg                                                    18

<210> SEQ ID NO 83
<211> LENGTH: 20
<212> TYPE: DNA
<213> ORGANISM: Vibrio parahaemolyticus
<220> FEATURE:
<221> NAME/KEY: prim_bind
<222> LOCATION: (1)..(20)

<400> SEQUENCE: 83
gattcgtttg acggacgcag                                                  20

<210> SEQ ID NO 84
<211> LENGTH: 40
<212> TYPE: DNA
<213> ORGANISM: Vibrio parahaemolyticus
<220> FEATURE:
<221> NAME/KEY: prim_bind
<222> LOCATION: (1)..(40)

<400> SEQUENCE: 84
ttcttagcgt attggagtcc catgttgatg acactgccag                            40

<210> SEQ ID NO 85
<211> LENGTH: 41
<212> TYPE: DNA
<213> ORGANISM: Vibrio parahaemolyticus
<220> FEATURE:
<221> NAME/KEY: prim_bind
<222> LOCATION: (1)..(41)

<400> SEQUENCE: 85
aatgtacagt attgcgtttt gcgatctctt cttgtgttga g                          41

<210> SEQ ID NO 86
<211> LENGTH: 20
<212> TYPE: DNA
<213> ORGANISM: Vibrio parahaemolyticus
<220> FEATURE:
<221> NAME/KEY: prim_bind
<222> LOCATION: (1)..(20)

<400> SEQUENCE: 86
caagcacttt cgcacgaatt                                                  20

<210> SEQ ID NO 87
<211> LENGTH: 18
<212> TYPE: DNA
<213> ORGANISM: Vibrio parahaemolyticus
```

```
<220> FEATURE:
<221> NAME/KEY: prim_bind
<222> LOCATION: (1)..(18)

<400> SEQUENCE: 87
aaagcgcctc agtttaag                                                   18

<210> SEQ ID NO 88
<211> LENGTH: 20
<212> TYPE: DNA
<213> ORGANISM: Vibrio parahaemolyticus
<220> FEATURE:
<221> NAME/KEY: prim_bind
<222> LOCATION: (1)..(20)

<400> SEQUENCE: 88
aagagcacgg tttcgtgaac                                                 20

<210> SEQ ID NO 89
<211> LENGTH: 40
<212> TYPE: DNA
<213> ORGANISM: Vibrio parahaemolyticus
<220> FEATURE:
<221> NAME/KEY: prim_bind
<222> LOCATION: (1)..(40)

<400> SEQUENCE: 89
ttcttagcgt attggagtcc gacatcaacc gctcatcgtc                           40

<210> SEQ ID NO 90
<211> LENGTH: 41
<212> TYPE: DNA
<213> ORGANISM: Vibrio parahaemolyticus
<220> FEATURE:
<221> NAME/KEY: prim_bind
<222> LOCATION: (1)..(41)

<400> SEQUENCE: 90
aatgtacagt attgcgtttt gcagaacaca aacttctcag c                         41

<210> SEQ ID NO 91
<211> LENGTH: 20
<212> TYPE: DNA
<213> ORGANISM: Vibrio parahaemolyticus
<220> FEATURE:
<221> NAME/KEY: prim_bind
<222> LOCATION: (1)..(20)

<400> SEQUENCE: 91
cggtgagttg ctgttgttgg                                                 20

<210> SEQ ID NO 92
<211> LENGTH: 18
<212> TYPE: DNA
<213> ORGANISM: Vibrio parahaemolyticus
<220> FEATURE:
<221> NAME/KEY: prim_bind
<222> LOCATION: (1)..(18)

<400> SEQUENCE: 92
atgtacaccc acgcattg                                                   18
```